United States Patent [19]

Mitsubayashi

[11] 3,991,213

[45] Nov. 9, 1976

[54] PESTICIDAL COMPOSITION

[75] Inventor: Takayoshi Mitsubayashi, Tokyo, Japan

[73] Assignees: Showa Denko Kabushiki Kaisha; Kokusai Eisei Kabushiki Kaisha, both of Tokyo, Japan

[22] Filed: May 27, 1975

[21] Appl. No.: 580,791

Related U.S. Application Data

[63] Continuation of Ser. No. 151,138, June 8, 1971, abandoned, which is a continuation-in-part of Ser. No. 829,794, June 2, 1969, abandoned.

[30] Foreign Application Priority Data

June 8, 1968  Japan................................ 43-38984

[52] U.S. Cl. ................................. 424/186; 424/219
[51] Int. Cl.$^2$............................................ A01N 9/08
[58] Field of Search............................ 424/186, 219

[56] References Cited
UNITED STATES PATENTS

| | | |
|---|---|---|
| 2,865,943 | 12/1958 | Lorenz................................ 424/219 |
| 3,160,556 | 12/1964 | Beaver et al........................... 424/84 |
| 3,248,288 | 4/1966 | Wilder et al............................ 424/83 |
| 3,318,769 | 5/1967 | Folckemer et al...................... 424/78 |
| 3,408,323 | 10/1968 | Hackney................................ 424/78 |
| 3,470,293 | 9/1969 | Geiger.................................... 424/84 |
| 3,608,062 | 9/1971 | Krefeld et al........................... 424/78 |

OTHER PUBLICATIONS

Merck Index 7th Edition (1960) pp. 263, 786, 874–875.

*Primary Examiner*—Norman A. Drezin
*Attorney, Agent, or Firm*—Wenderoth, Lind & Ponack

[57] ABSTRACT

Pesticidal composition capable of gradual exhalation of the vapors of enhanced synergistic insecticidal activity at ordinary temperature, which comprises a very slightly volatile pesticide, a volatile organophosphorus pesticide and a polymer of vinyl series compound together with the auxiliary additives.

Vapor of the volatile insecticide serves to entrain a minor amount of vapor of the very slightly volatile pesticide, while the polymer of the vinyl series compound serves as a carrier base for the pesticides.

6 Claims, No Drawings

PESTICIDAL COMPOSITION

This application is a continuation of application Ser. No. 151,138, filed June 8, 1971 (now abandoned) which, in turn, is a continuation-in-part of application Ser. No. 829,794, filed June 2, 1969 (now abandoned).

This invention relates to an insecticidal or pesticidal composition capable of gradual exhalation of the insecticidally active vapors at an ordinary temperature for an extended time.

More particularly, the present invention relates to the pesticidal composition comprising (A) the pesticidal ingredients in combination of (a) a volatile organophosphate as essential pesticide selected from the group consisting of dimethyl 2,2-dichlorovinyl phosphate (DDVP), diethyl 2,2-dichlorovinyl phosphate, dimethyl 1,2-dibromo-2,2-dichloroethyl phosphate (DIBROM) and dimethyl 2-carbomethoxy-1-methylvinyl-phosphate (PHOSDRIN) and (b) a slightly volatile pesticide selected from the group consisting of natural and synthetic pyrethroids and perillaldehyde and (B) a carrier base selected from the group consisting of chlorinated polyethylene, chlorinated polypropylene, polychloroprene, polyvinyl acetate, polyvinyl chloride, ethylenevinyl chloride copolymer, chlorinated ethylene-propylene copolymer, and polymer of ethylene-vinyl acetate grafted with vinyl chloride.

In the composition of the present invention, the vapor gradually volatilized at ordinary temperature from the specified organophosphates serves as a vaporization promoter of the less volatile pesticides.

It was known that the afore-mentioned DDVP, diethyl 2,2-dichlorovinyl phosphate, Dibrom and Phosdrin used as one of the pesticidal agents in the composition of the present invention exhibit an outstanding insecticidal activity to various pests in adult and nymphal stages.

Pyrethrin and cinerin have widely been used as powerful insecticides, while perillaldehyde and its derivatives such as the alpha-antioxime are also known as insecticides.

Since these very slightly volatile pesticides are liquid or solid substances difficult to vaporize at ordinary temperatures, they are usually employed as pest-combatting agents in the form of dusting compositions, aqueous emulsions or organic solutions for spraying purposes and fumigating preparations such as the mosquito coil.

The active agents contained in the dusting compositions, aqueous emulsions and organic solutions, when spread by dusting or spraying, do not gasify much, if at all, and under the circumstances, they do not sufficiently display their peculiar pesticidal activities.

The fumigating preparations, on the other hand, have a drawback that most part of the active agent contained therein is wasted due to burning and/or thermal decomposition when used. Only a fraction, say at the most about 20–30%, of the total content of the active agent in the preparation is generally available as effective insecticide.

Now, it has been observed that the afore-mentioned volatile pesticides are compatible with the said very slightly volatile pesticides and that the vapor of the volatile pesticide give off at ordinary temperatures diffuses into the atmosphere carrying with it a minute amount of the vapor of the said very slightly volatile pesticide when the latter are brought into intimate contact with the former. The fact may be regarded as comparable to the phenomenon that occurs when a sparingly volatile substance is subjected to steam distillation.

It is surprising that the pesticidal composition of the present invention, which contains both the volatile and slightly volatile insecticides exhibits an extraordinary and rapid pesticidal activity superior to those exhibited by the respective active agents contained in the hitherto known pesticidal compositions.

DDVP, diethyl-2,2-dichlorovinyl phosphate, Dibrom, Phosdrin and the like used in the composition of the present invention are known substances which possess a high pesticidal activity and a fairly rapid vaporizing tendency at ordinary temperatures. They vaporize off within a relatively short time when applied in the form of a dusting or spraying preparation such as an aqueous emulsion. Repeated applications of the preparation are therefore required in order to maintain a durable efficacy.

Other pesticidal compositions have been proposed in which pesticidal compounds such as DDVP and the like are incorporated into a polymer base. An improved durable activity of the finished composition is thus obtained.

The present invention is concerned with an improvement of the last mentioned known pesticidal compositions.

The pesticidal composition of the present invention is characterized by the presence of about 2–15% by weight of the aforementioned slightly volatile pesticide as the secondary active ingredient, based on the weight of the afore-mentioned volatile organophosphorus pesticide carried on the polymer base in accordance with the known arts. Using the composition of the present invention, there is thus obtained an enhanced insecticidal activity on insects such as mosquitoes, flies, mites and the like.

Although the mechanism of the conjoint pesticidal activity represented by the active agents contained in the composition of the present invention is not well understood, and I accordingly do not stand firmly to the opinion, it is postulated that the insects such as mosquitoes are rapidly killed by a synergistic or conjoint insecticidal activity of the mixed vapors of the volatile insecticide and the slightly volatile insecticide.

The pyrethroid used as the auxiliary or secondary pesticide in formulation of the pesticidal composition includes the natural pyrethroids such as pyrethrin I, pyrethrin II, cinerin I and cinerin II, as well as the synthetic pyrethroids such as allethrin, Furethrin, cyclethrin, barthrin, dimethrin, benathrin and phthalthrin, all of which are of scarcely volatile at ambient temperature.

In order to ensure an enhanced blendability and processibility of the composition as well as a controlled gradual volatilization of the active agents from the established composition, use of a chlorinated polyethylene having 20–45% by weight of chlorine content as the carrier base is preferable.

The total composition comprises about 10% to 30% by weight of combined insecticides, preferably 15% to 25%, and the carrier base can have additives such as plasticizer, filler, perfume and the like.

It is worthy of notice that an even evaporation rate of the vapors of the active agents from the composition and also an effective protection from chemical change of the active agents, caused by the hydrogen chloride that is the result of a partial decomposition of the chlorinated polyethylene, can advantageously be effected by the addition of an amount of epoxy resin to the carrier base which contains stabilizer, lubricating agent and plasticizer adapted for the polymers of the chlorine-containing vinyl compounds.

The preparation of the pesticidal compositions of the present invention may be performed in accordance with conventional procedures.

Since the mixture of the active agents used in the composition shows a pronounced compatibility with the abovementioned carrier bases, the making of the composition may readily be achieved by a simple mechanical blending of the pulverized polymer and a mixture of the active agents together with other auxiliary additives. The composition may be shaped, for example, by milling on rolls, moulding, extruding, casting and the like into sheets, rods, granular pellets and the like of the plastic. In particular, the composition which contains a chlorinated polyethylene having a chlorine content within the range of 20–45% by weight can advantageously be moulded even at ordinary temperatures or a slightly elevated temperature.

In the commercial production of the shaped plastic of the composition, it is advisable to feed the powdery composition to a suitably heated extruder and after continuously extruding the molten mass through an aperture to form a belt, to then quench and cut it into pieces having a desired dimension.

Although there is no particular limitation with respect to the fields of application of the composition of the present invention, the same may advantageously be applied for the purpose of exterminating the insects and pests in living room, food- or garment-warehouse, granary, horticultural green house, cargo hold and the like.

The performance of the insecticidal composition of the present invention will be illustrated by the following Examples.

EXAMPLE 1

A batch was prepared by blending the following ingredients.

| Ingredients | Parts by weight |
| --- | --- |
| Pyrethrin | 2.0 |
| Dimethyl 2,2-dichlorovinyl phosphate | 30.0 |
| Chlorinated polyolefine having 35% Cl-content | 100.0 |
| Dioctyl phthalate (D O P) | 40.0 |
| Epoxy rosin | 10.0 |
| Calcium stearate (stabilizer) | 5.0 |
| Calcined Magnesia | 20.0 |

The batch was divided into fractions each having about 120 grams and charged into a series of the rectangular metallic pans having the dimensions of 65 mm width, 10 mm depth and 220 mm length. The pens were held at a temperature of 150°–160° C. for about 10–12 minutes. The melted batches were then quenched to room temperature. There were obtained pliant plastic pieces each having the dimension of 65 mm width, 7 mm thickness and about 220 mm length, and weighing about 120 grams.

The insecticidal activity of the pieces was tested as follows:

1. Pests under tests:
    a. Adult house flies, *Musca vicina*, were raised with a liquor containing 5% of dry milk and 5% of cane sugar for 5 days, the house flies before breeding being at the stage of just an emergence of larvae grown on bean-curds waste in a thermostat kept at the temperature of 27° C.
    b. Adult under-ground house mosquitoes, *Culex pipiens molestus*, sensitive to insecticides such as pyrethrin, were used which were raised for 5 days on a sheet of cotton gauze impregnated with a 5% aqueous cane sugar solution. The mosquitoes were a stage of just emergence of larvae grown in well water containing Ebios, a yeast extract.

2. Pieces under tests:
    a. The fresh plastic obtained in the Example
    b. The plastic after a one month exposure to the ambient atmosphere
    c. The plastic after a two month exposure to the ambient atmosphere
    d. The plastic after a three month exposure to the ambient atmosphere.

3. Method of tests:
    6 grams of small cubic fragments of each of the abovementioned four test plastics were separately filled in four mesh bags. The bags were separately suspended at the centers of four empty boxes of 1 cubic meter capacity, each provided with three vertical glass walls.
    50 Adult flies and 25 adult mosquitoes aforementioned were released in each of the boxes and the behavior of the flies, that is, the flies that came down, reversed and passed away, were observed and counted in the intervals of the time to obtain the mortalities thereof.

4. Mortality of the house flies observed:

| Time elapsed (minutes) | Mortalities (%) of Flies Caused by Plastics | | | |
| --- | --- | --- | --- | --- |
| | (a) | (b) | (c) | (d) |
| 5 | 10.0 | 8.0 | 6.0 | 2.0 |
| 10 | 26.7 | 14.0 | 12.0 | 10.0 |
| 15 | 43.3 | 34.0 | 32.0 | 30.0 |
| 20 | 66.7 | 64.0 | 66.0 | 38.0 |
| 25 | 93.3 | 80.0 | 80.0 | 66.0 |
| 30 | 100.0 | 90.0 | 92.0 | 92.0 |
| 35 | — | 100.0 | 100.0 | 98.0 |
| 40 | — | — | — | 100.0 |

5. Mortality of the mosquitoes observed:

| Time elapsed (minutes) | Mortalities (%) of Mosquitoes Caused by Plastics | |
| --- | --- | --- |
| | (a) | (control)* |
| 5 | 12.0 | 12.0 |
| 10 | 72.0 | 60.0 |
| 15 | 80.0 | 76.0 |
| 20 | 100.0 | 88.0 |
| 25 | — | 100.0 |

*Fragments of the plastic of the composition without pyrethrin, prepared in accordance with the Example.

Mortalities of the mosquitoes caused by the fragments of the plastics (b), (c) and (d) were almost the same as those of the plastic (a).

EXAMPLE 2

A batch of the following formulations was shaped into pieces of plastic in accordance with the preceding Example.

| Ingredients | Parts by weight |
|---|---|
| Pyrethrin | 2.5 |
| Diethyl 2,2-dichlorovinyl phosphate | 35.0 |
| Chlorinated polyethylene having 32% Cl-content | 100.0 |
| D O P | 40.0 |
| Epoxy resin | 10.0 |
| Calcium stearate (stabilizer) | 1.0 |
| Lead trihydrogen phosphate (Stabilizer) | 2.5 |
| Diatomaceous earth | 20.0 |

Each of the shaped pieces thus obtained had the same dimension and weight as those of the pieces obtained in the preceding Example.

The pieces were placed in mesh bags made of polyethylene and suspended in a proportion of a bag per 50 m³ space of a horticultural green house of 396 m² area. In the green house, carnations were planted which were infested with a lot of aphids.

After three days' exposure, it was found that all the aphids were killed.

EXAMPLE 3

A batch of the following formulation was shaped into pieces in accordance with the preceding Example.

| Ingredients | Parts by weight |
|---|---|
| Pyrethrin | 3.0 |
| Dimethyl 2,2-dichlorovinyl phosphate | 20.0 |
| Chlorinated polyethylene having 35% Cl-content | 100.0 |
| D O P | 50.0 |
| Chlorinated paraffin | 10.0 |
| Lead phthalate (stabilizer) | 3.5 |
| Precipitated calcium carbonate | 15.0 |
| Brown pigment | 1.0 |

Each of the shaped pieces thus obtained had the same dimension and weight as those of the pieces obtained in the preceding Example.

The pieces were placed in mesh bags of polyethylene and suspended in a proportion of one bag per 40 cubic meter space of a horticultural green house of 198 m² area. In the green house, carnations were planted which were infested with a lot of mites. After two days' exposure, it was found that all the mites were killed.

EXAMPLE 4

To 80 parts of a blend consisting of 0.5 parts of perillaldehyde, 19.5 parts of DDVP and 80 parts of chlorinated polyethylene having the 35% chlorine content were added 2 parts of Neo Base (basic lead sulfite) as stabilizer. The whole was well mixed by stirring at room temperature and then extruded through an aperture of the extruder at 180° C. to form a belt having about 7 mm thickness and about 75 mm width.

A test piece weighing about 6 grams and having about 12 mm length was cut off from the belt which was then fixed on the glass ceiling of a glass cylinder having a 20 cm inner diameter and 43 cm height.

At the center of the glass bottom of the cylinder, a cage of wire gauze containing 30 adult Azuki-bean weevils was placed, the weevils having been raised for 5 days with a 5% aqueous cane sugar solution just after emergence of the larvae.

The temperature of the inside space of the cylinder was kept at 25° C., and the behavior of the weevils under test was observed, that is, the numbers of the pests that came down, reversed and passed away after the lapse of the time were counted and finally the mortality thereof was inspected.

For the sake of comparison, the same observation was carried out with a test piece of plastic prepared in accordance with the above-mentioned procedure with a batch of the same composition as that above-mentioned except that perillaldehyde was absent and 20 parts of DDVP in lieu of 19.5 parts thereof was contained.

The mortalities of the weevils in the two cases thus observed were tabulated.

| Times (hrs.) for Exposure | Mortalities (%) | |
|---|---|---|
| | Test Piece A* | Test Piece B** |
| 15 | 6.7 | 3.3 |
| 20 | 23.3 | 10.0 |
| 30 | 46.7 | 23.3 |
| 40 | 60.0 | 40.0 |
| 60 | 86.7 | 63.3 |
| 80 | 96.7 | 83.3 |
| 120 | 100.0 | 96.7 |
| 150 | — | 100.0 |

*Test piece of the plastic according to the instant Example.
**Test piece of the plastic for the comparison.

EXAMPLE 5

A composition was prepared by stirring a formulation of the following ingredients.

| Ingredients | Parts by weight |
|---|---|
| Cinerin | 1 |
| Dimethyl-1,2-dibromo-2,2-dichloroethyl phosphate | 30 |
| Pulverized polyvinyl chloride | 100 |
| D O P | 40 |
| Calcium stearate | 5 |
| Magnesia | 20 |

The batch was kneaded on open rolls at 80° C. to form a continuous sheet.

A control sheet was prepared in analogous manner from a batch without cinerin and containing 31 parts of dimethyl-1,2-dibromo-2,2-dichloroethyl phosphate and the same parts of the other ingredients as those used in the above-mentioned composition.

6 grams of each of these two sheets was hung respectively on the ceiling of a cubic glass vessel of 0.5 m³ capacity.

In each vessel kept at 25° C., 30 adult Takatsuki strain house flies were released and the numbers of flies that came down and reversed in a course of time were inspected.

The percent of the reversed flies was listed.

| Times (hrs.) for Exposure | Reversed flies (%) | |
|---|---|---|
| | Test Piece A* | Test Piece B** |
| 5 | 6.7 | 3.3 |
| 10 | 20.0 | 6.7 |
| 15 | 43.3 | 20.0 |
| 20 | 60.0 | 43.3 |
| 25 | 86.7 | 60.0 |

-continued

| Times (hrs.) for Exposure | Reversed flies (%) | |
|---|---|---|
| | Test Piece A* | Test Piece B** |
| 30 | 100.0 | 83.3 |
| 35 | — | 93.3 |
| 40 | — | 100.0 |

*Test piece of the plastic according to the instant Example.
**Test piece of the plastic for the comparison.

EXAMPLE 6

A composition was prepared by blending the following ingredients.

| | Parts by weight |
|---|---|
| Pyrethrin | 2 |
| Graft polymer* | 100 |
| D O P | 20 |
| Neo Base (basic lead sulfite) | 5 |
| Phosdrin | 30 |

*A graft polymer of equal parts by weight of vinyl chloride and a copolymer of ethylene : vinyl acetate (50 : 50)

For the sake of comparison, another composition was prepared by blending the ingredients same as those above-mentioned with exception that pyrethrin was absent and 32 parts of phosdrin was present.

6 grams of each of the two compositions were separately enveloped with a sheet of thin cotton gauze and suspended at the centers of two empty wooden boxes of 1 cubic meter capacity provided with three vertical glass walls.

50 adult under-ground house mosquitoes, *Culex pipiens Molestus*, which were raised for 5 days on a sheet of cotton gauze impregnated with the 5% aqueous cane sugar solution, were released in each box.

The mosquitoes were at a stage of just an emergence of larvae grown in a well water containing Ebios, a yeast extract.

The behavior of the mosquitoes in the boxes at 25° C. was observed to inspect the killing effect of the compositions.

The result of the observations were listed.

| Times (Minutes) for Exposure | Mortalities (%) of Mosquitoes | |
|---|---|---|
| | Composition A* | Composition B** |
| 5 | 14 | 8 |
| 10 | 44 | 22 |
| 15 | 82 | 32 |
| 20 | 96 | 56 |
| 25 | 100 | 74 |
| 30 | — | 92 |
| 40 | — | 100 |

*Composition according to the instant Example
**Composition for the comparison

EXAMPLE 7

A sheet was prepared by milling on rolls a composition of the following formulation.

| | Parts by weight |
|---|---|
| Perillaldehyde | 3.0 |
| Dimethyl 2,2-dichlorovinyl phosphate | 30.0 |
| Chloroprene | 100.0 |
| D O P | 30.0 |
| Neo Base (basic lead sulfite) | 5.0 |

A control sheet was prepared in analogous manner with a composition free from perillaldehyde and containing 33 parts of dimethyl 2,2-dichlorovinyl phosphate and the same parts of the other respective ingredients as those used in the above-mentioned formulation.

Pesticidal activities of these sheets were inspected with 50 adult Takatsuki strain house flies under same conditions as those employed in the tests given in Example 5.

The results obtained were listed.

| Times (Minutes) for Exposures | Mortalities (%) | |
|---|---|---|
| | Test piece A* | Test piece B** |
| 5 | 18 | 6 |
| 10 | 52 | 12 |
| 15 | 90 | 28 |
| 20 | 96 | 50 |
| 25 | 100 | 68 |
| 30 | — | 90 |
| 35 | — | 98 |
| 40 | — | 100 |

*Composition according to the instant Example
**Composition for the comparison

The pieces of the two plastics each weighing about 120 grams were separately placed in mesh bags made of polyethylene. The bags were independently hung on the ceiling of a granary in a proportion of one bag per 150 m³ space.

It was found that growth of rice weevils was completely prevented.

EXAMPLE 8

A composition was prepared by blending the following ingredients.

| | Parts by weight |
|---|---|
| Pyrethrin | 1 |
| Dimethyl dibromovinyl phosphate | 25 |
| Ethylene-vinyl chloride copolymer | 100 |
| D O P | 20 |
| Neo Base (basic lead sulfite) | 5 |

The composition in a mesh bag made of polyethylene was hung on the ceiling of a garment warehouse.

The garments were completely prevented from damage caused by larvae of the clothes moth.

EXAMPLE 9

Eight test pieces I – VIII each having 4 cm width, 12 cm length and 3 mm height were prepared from each of 200 parts of the following formulations in accordance with the preceding Examples:

| | Parts by weight |
|---|---|
| Pyrethroid* | 5 |
| Dimethyl-2,2-dichlorovinyl phosphate | 40 |

-continued

| | Parts by weight |
|---|---|
| Chlorinated polyethylene having 32% by weight of chlorine | 100 |
| DOP | 30 |
| Basic lead sulfite | 5 |

*In Test Piece I: Pyrethrin I
In Test Piece II: Allethrin
In Test Piece III: Furethrin
In Test Piece IV: Cyclethrin
In Test Piece V: Barthrin
In Test Piece VI: Dimethrin
In Test Piece VII: Benathrin, and
In Test Piece VIII: Phthalthrin
are respectively employed.

Another test piece IX was also prepared as control from the formulation containing no D D V P as follows:

| | Parts by weight |
|---|---|
| Pyrethrin I | 45 |
| Chlorinated polyethylene having 32% by weight of chlorine | 100 |
| D O P | 30 |
| Basic lead sulfite | 5 |

Pesticidal activities of test pieces I – VIII and the control piece IX were inspected in accordance with the method given in Example 6 with under-ground house mosquitoes, *Culex pipiens molestus*.

The results observed were listed.

| | Mortalities (%) of Mosquitoes | | | | | | |
|---|---|---|---|---|---|---|---|
| Time (minutes) | 5 | 10 | 15 | 20 | 25 | 30 | 60 |
| Test Pieces | | | | | | | |
| I | 15 | 40 | 81 | 93 | 100 | — | — |
| II | 23 | 56 | 85 | 100 | — | — | — |
| III | 3 | 11 | 25 | 41 | 60 | 81 | 100 |
| IV | 9 | 19 | 37 | 64 | 89 | 100 | — |
| V | 11 | 36 | 52 | 78 | 93 | 100 | — |
| VI | 18 | 44 | 79 | 100 | — | — | — |
| VII | 12 | 26 | 49 | 54 | 77 | 86 | 100 |
| VIII | 2 | 11 | 26 | 33 | 61 | 86 | 100 |
| IX (control) | — | — | — | — | — | 1 | 1 |

As is evident from the above, the compositions containing synthetic pyrethroids showed pesticidal activities comparable to those shown by compositions containing natural pyrethroids. Contrary to the above, it is noted that the test piece IX showed almost no pesticidal activity. This proves that pyrethrin I in the composition could not vaporize at all in the absence of a volatile pesticidal agent such as D D V P.

What is claimed is:

1. An insecticidal composition comprising (A) about 10 – 30 percent by weight of a mixture consisting of (a) a volatile organophosphate selected from the group consisting of dimethyl 2,2-dichlorovinyl phosphate, diethyl 2,2-dichlorovinyl phosphate, dimethyl 1,2-dibromo-2,2-dichloroethyl phosphate and dimethyl 2-carbomethoxy-1-methylvinyl phosphate, and (b) at least one member of the group consisting of (1) a natural pyrethroid selected from the group consisting of pyrethrins I and II and cinerins I and II, (2) a synthetic pyrethroid selected from the group consisting of allethrin, furethrin, cyclethrin, barthrin, dimethrin, benathrin and phthalthrin, and (3) perillaldehyde and (B) about 70 – 90 percent by weight of a carrier selected from the group consisting of chlorinated polyethylene, chlorinated polypropylene, polychloroprene, polyvinyl acetate, polyvinyl chloride, ethylene-vinyl chloride copolymer, chlorinated ethylene-propylene copolymer and polymer of ethylene-vinyl acetate grafted with vinyl chloride, wherein the approximate proportion between said volatile organophosphate to said pyrethroids or perillaldehyde is 100 : 2–15 by weight.

2. A composition according to claim 1 wherein the pyrethroid (b) is perillaldehyde.

3. A composition according to claim 1 wherein the volatile organophosphate is dimethyl-2,2-dichlorovinyl phosphate.

4. A composition according to claim 1 wherein the carrier is chlorinated polyethylene.

5. A composition according to claim 1 wherein the carrier is polychloroprene.

6. A composition according to claim 1 wherein the carrier is the ethylene-vinyl acetate copolymer grafted with vinyl chloride.

* * * * *